United States Patent
Kim et al.

(10) Patent No.: US 11,939,338 B2
(45) Date of Patent: Mar. 26, 2024

(54) SPIROPYRAN COMPOSITE HAVING IMPROVED MECHANO-SENSITIVITY, METHOD FOR MANUFACTURING THE SAME, AND CHROMIC ARTICLE INCLUDING THE SAME

(71) Applicant: KOREA INSTITUTE OF SCIENCE AND TECHNOLOGY, Seoul (KR)

(72) Inventors: Jaewoo Kim, Jeollabuk-do (KR); Jun Young Jo, Jeollabuk-do (KR); Yong Chae Jung, Jeollabuk-do (KR); Yong Seok Choi, Jeollabuk-do (KR); Han Gyeol Jang, Jeollabuk-do (KR); Sungmin Jung, Jeollabuk-do (KR); Dong Woo Kim, Jeollabuk-do (KR)

(73) Assignee: Korea Institute of Science and Technology, Seoul (KR)

(*) Notice: Subject to any disclaimer, the term of this patent is extended or adjusted under 35 U.S.C. 154(b) by 214 days.

(21) Appl. No.: 17/228,109

(22) Filed: Apr. 12, 2021

(65) Prior Publication Data

US 2022/0162223 A1    May 26, 2022

(30) Foreign Application Priority Data

Nov. 26, 2020  (KR) .......................... 10-2020-0161580

(51) Int. Cl.
    C09K 9/02    (2006.01)
    C07D 491/107    (2006.01)
    C08L 83/04    (2006.01)
(52) U.S. Cl.
    CPC .......... *C07D 491/107* (2013.01); *C08L 83/04* (2013.01); *C09K 9/02* (2013.01); *C09K 2211/1033* (2013.01)

(58) Field of Classification Search
    CPC ........ C07D 491/107; C09K 2211/1033; C09K 9/02; C08L 83/04
    See application file for complete search history.

(56) References Cited

FOREIGN PATENT DOCUMENTS

| KR | 10-1134224 B1 | 4/2012 |
| KR | 1020180055081 A | 5/2018 |

OTHER PUBLICATIONS

Dong Woo Kim, Grigori A. Medvedev, James M. Caruthers, Jun Young Jo, You-Yeon Won, and Jaewoo Kim, Enhancement of Mechano-Sensitivity for Spiropyran-Linked Poly(dimethylsiloxane) via Solvent Swelling, Macromolecules 2020, 53, 7954-7961 (Year: 2020).*

(Continued)

*Primary Examiner* — Bijan Ahvazi
(74) *Attorney, Agent, or Firm* — Rabin & Berdo, P.C.

(57) ABSTRACT

The present disclosure relates to a spiropyran composite having improved mechano-sensitivity, a method for manufacturing the same, and a chromic article including the same. Particularly, the spiropyran composite is obtained by bonding spiropyran covalently to a polymer, an inorganic material or a mixture thereof to form spiropyran composite, and impregnating the spiropyran composite with a sensitivity-enhancing agent for a suitable time through a wet infiltration process to form non-polar environment at the inner part of the spiropyran composite, to cause pre-stretch and to increase a change in color or fluorescence in response to force, stress or strain, thereby providing significantly improved mechano-sensitivity. In addition, a wet filtration process is used and no expensive equipment is required to simplify the process. Further, the process can be performed rapidly within several minutes to reduce the processing time.

11 Claims, 7 Drawing Sheets

(56) References Cited

OTHER PUBLICATIONS

Gregory R. Gossweiler, Gihan B. Hewage, Gerardo Soriano, Qiming Wang, Garrett W. Welshofer, Xuanhe Zhao, and Stephen L. Craig, Mechanochemical Activation of Covalent Bonds in Polymers with Full and Repeatable Macroscopic Shape Recovery, ACS Macro Lett. 2014, 3, 216-219 (Year: 2014).*

C. V. Rumens, M. A. Ziai, K. E. Belsey, J. C. Batchelor and S. J. Holder, Swelling of PDMS networks in solvent vapours; applications for passive RFID wireless sensors, J. Mater. Chem. C, 2015, 3, 10091-10098. (Year: 2015).*

Corissa K. Lee et al., "Solvent Swelling Activation of a Mechanophore in a Polymer Network", American Chemical Society, Macromolecules 2014, 47, 8, pp. 2690-2694, Publication Date: Apr. 4, 2014.

Dong Woo Kim et al., "Enhancement of Mechano-Sensitivity for Spiropyran-Linked Poly(dimethylsiloxane) via Solvent Swelling", Macromolecules, vol. 53, pp. 7954-7961, Sep. 10, 2020.

* cited by examiner spriopyran (SP) form   merocyanine (MC) form

Compression
(250 N)

Before impregnation

Impregnation for
15 minutes

Before impregnation

Impregnation for 15 minutes

SPIROPYRAN COMPOSITE HAVING IMPROVED MECHANO-SENSITIVITY, METHOD FOR MANUFACTURING THE SAME, AND CHROMIC ARTICLE INCLUDING THE SAME

CROSS-REFERENCE TO RELATED APPLICATIONS

This application claims priority under 35 U.S.C. § 119 to Korean Patent Application No. 10-2020-0161580 filed on Nov. 26, 2020 in the Korean Intellectual Property Office, the disclosure of which is incorporated herein by reference in its entirety.

TECHNICAL FIELD

The following disclosure relates to a spiropyran composite having significantly improved sensitivity to mechanical stimulation, such as force, stress or strain, a method for manufacturing the same, and a chromic article including the same.

BACKGROUND

Spiropyran (SP) is a molecular sensor showing a change in color or fluorescence in response to force, and a self-monitoring smart material capable of detecting strain, stress and damage can be obtained by coupling spiropyran with an organic or inorganic material. A spiropyran self-monitoring material is a smart material capable of detecting damage autonomously, and is advantageous in that it requires no external equipment and power source, allows continuous and active monitoring, and is less affected by external environment, such as temperature and humidity. Such a spiropyran self-monitoring material has been given many attentions as a material having high potential applicability in the fields of stress and strain sensors, detection of damage, artificial skin, or the like.

Meanwhile, there have been largely used to date contact monitoring methods based on piezoelectric sensors, linear variable differential transformer (LVDT), accelerometer or GPS, or non-contact monitoring methods based on LiDAR photographing in order to detect stress or strain and damage. However, such conventional methods can perform detection with the proviso that external power is supplied continuously thereto, and whether any damage occurs or not can be determined by professionally trained experts through the results of signal processing. Therefore, a large amount of human and material resources is required.

On the contrary, a spiropyran self-monitoring material is advantageous in that it requires no external equipment and power source, allows continuous and active monitoring, and is less affected by external environment, such as temperature, humidity, or the like. In addition, general people can also play a role in detection and analysis.

However, a spiropyran self-monitoring material is problematic in that it has low mechano-sensitivity. For example, in the case of a silicone or polyurethane material to which spiropyran is introduced, it is not possible to observe a change in color/fluorescence until 50% of the silicone material or 500% of the polyurethane material is deformed. In other words, there is an imminent need for studies about improvement of such low mechano-sensitivity in order to apply the spiropyran material practically.

Two methods have been studied to increase the mechano-sensitivity of a spiropyran material. The first method is a method for improving the mechano-sensitivity through a change in chemical structure of the spiropyran molecule itself. For example, the sensitivity can be improved significantly by modifying the binding position of a functional group in the molecule, number of functional groups and electronegativity. The second method is a method for improving the mechano-sensitivity by maximizing the efficiency of transferring external force to a spiropyran molecular sensor. In other words, some reports have been disclosed about improvement of the mechano-sensitivity by 560% through the introduction of ultramolecular interaction, polymer chain alignment and a geometric microstructure in the material structure. However, there has been no report about a method using a wet infiltration process for improving such low mechano-sensitivity of a spiropyran self-monitoring material.

REFERENCES

Patent Documents (Patent Document 1) Korean Patent Publication No. 10-1134224

SUMMARY

The present disclosure is designed to solve the problems of the related art, and an embodiment of the present disclosure is directed to providing a spiropyran composite having significantly improved mechano-sensitivity.

The present disclosure is also directed to providing a chromic article including the spiropyran composite.

In addition, the present disclosure is directed to providing a method for manufacturing a spiropyran composite including a simple process and providing a reduced processing time by using a wet infiltration process.

In one aspect of the present disclosure, there is provided a spiropyran composite including: spiropyran; and a polymer, an inorganic material or a mixture thereof covalently bound to the spiropyran, and further including a sensitivity-enhancing agent to mechanical stimulation with which the inner part or the surface of the spiropyran composite is impregnated partially or totally.

In another aspect of the present disclosure, there is provided a chromic article including the spiropyran composite.

In still another aspect of the present disclosure, there is provided a method for manufacturing a spiropyran composite, including the steps of: introducing spiropyran to a polymer, an inorganic material or a mixture thereof and carrying out curing to obtain a spiropyran composite in which a covalent bond is induced; and impregnating the inner part or the surface of the spiropyran composite partially or totally with a sensitivity-enhancing agent to mechanical stimulation by using a wet infiltration process.

The spiropyran composite according to the present disclosure is obtained by bonding spiropyran covalently to a polymer, an inorganic material or a mixture thereof to form spiropyran composite, and impregnating the spiropyran composite with a sensitivity-enhancing agent for a suitable time through a wet infiltration process, and thus shows significantly improved mechano-sensitivity as compared to the conventional spiropyran self-monitoring materials.

In addition, the method for manufacturing a spiropyran composite according to the present disclosure includes impregnating a spiropyran composite with a sensitivity-enhancing agent through a wet filtration process, and thus requires no expensive equipment, includes a simple process, and can be performed rapidly within several minutes to reduce the processing time. Further, the inner part of the spiropyran composite can be provided with non-polar environment by controlling the time of impregnation with the sensitivity-enhancing agent to cause pre-stretch and to increase a change in color or fluorescence in response to force, stress or strain, thereby providing significantly improved mechano-sensitivity.

The scope of the present disclosure is not limited to the above-mentioned effects. It should be understood that the effects of the present disclosure cover all of the effects inferable from the following description.

DETAILED DESCRIPTION OF EMBODIMENTS

Hereinafter, various aspects and embodiments of the present disclosure will be explained in more detail.

The present disclosure relates to a spiropyran composite having significantly improved sensitivity to mechanical stimulation, such as force, stress or strain, a method for manufacturing the same, and a chromic article including the same.

As described above, the conventional spiropyran self-monitoring materials cannot show a change in color or fluorescence until they are deformed to a high level (50% or more), and thus are limited in their application.

Under these circumstances, according to the present disclosure, a polymer, an inorganic material or a mixture thereof is bound covalently to spiropyran to form a spiropyran composite, and the spiropyran composite is impregnated with a sensitivity-enhancing agent for a suitable time through a wet infiltration process, thereby providing significantly improved mechano-sensitivity as compared to the conventional spiropyran self-monitoring materials.

In addition, the spiropyran composite according to the present disclosure has controllable mechano-sensitivity through the control of the impregnation time by using a wet infiltration process, requires no expensive equipment, includes a simple process, and can be obtained rapidly within several minutes to reduce the processing time. Particularly, such an effect of improving mechano-sensitivity may be realized by impregnating the inner part of the spiropyran composite with a sensitivity-enhancing agent to form non-polar environment, to cause pre-stretch and to increase a change in color or fluorescence in response to strain.

Particularly, in one aspect of the present disclosure, there is provided a spiropyran composite including: spiropyran; and a polymer, an inorganic material or a mixture thereof covalently bound to the spiropyran, and further including a sensitivity-enhancing agent to mechanical stimulation with which the inner part or the surface of the spiropyran composite is impregnated partially or totally.

Spiropyran shows self-chromic and fluorescence properties in response to external stimulation, such as force, stress or strain, and provides an effect of detecting damage autonomously without any separate external equipment and power source. In addition, spiropyran is advantageous in that it can be synthesized as a cost-efficient and very stable material depending on combination with another material, is combined with a polymer, an inorganic material, or the like, to be processed easily into various shapes, and is not harmful to the human body.

Figure 1:
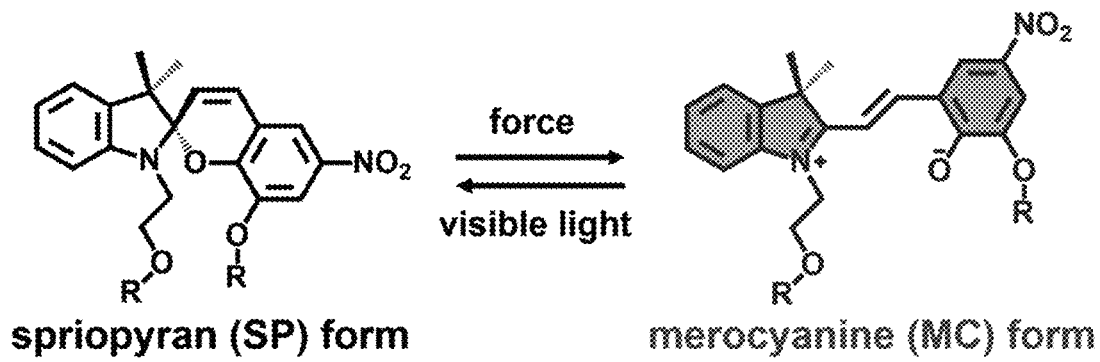
FIG. 1 shows a change in chemical structure of a spiropyran molecule caused by external stimulation (force, stress, strain).

FIG. 1 shows a change in chemical structure of a spiropyran molecule caused by external stimulation (force, stress, strain). Referring to FIG. 1, when mechanical force (strain, stress or damage) is applied to spiropyran, a significant change in color and fluorescence properties occurs, while spiropyran (left) undergoes a change in chemical structure into merocyanine (right) through a selective ring-opening reaction of C—O bond in the molecule. While spiropyran is colorless or shows a light yellow color and realizes little fluorescence, merocyanine shows a purple or blue color and realizes fluorescence in a wavelength region of 550-700 nm. In addition, the merocyanine molecule causes a ring-closing reaction upon the irradiation of visible rays, and then is converted back into spiropyran (left).

Such a clear difference in optical properties between spiropyran (SP) and merocyanine (MC) is advantageous in that it can be detected through an optical device and can be seen easily by the naked eyes with no separate device. In addition, when irradiating visible rays, reversibility of conversion from merocyanine (MC) back into spiropyran (SP) allows the use as a permanent sensor.

The polymer, the inorganic material or mixture thereof can be bound covalently to the chemical structure of spiropyran to form a spiropyran composite. When they are linked through covalent bonding, transfer of force, stress or strain from the outside can be performed efficiently to shows a change in color or fluorescence. In addition, the polymer, the inorganic material or mixture thereof can be bound to spiropyran and mixed to be processed into articles having various shapes with a three-dimensional structure or self-monitoring smart materials.

The polymer may be at least one selected from the group consisting of polydimethyl siloxane, polyurethane, polycaprolactone, polyamide, polystyrene, polyacrylate, polyaniline, epoxy, cellulose, natural rubber and derivatives thereof, but is not limited thereto. Particularly, the polymer may be at least one selected from the group consisting of polydimethyl siloxane, polyurethane and polycaprolactone, and more particularly the polymer may be polydimethyl siloxane.

The inorganic material may be a hydride or oxide including at least one selected from the group consisting of iron, aluminum, copper, tin, boron and silicon, but is not limited thereto. Particularly, the inorganic material may be aluminum or silicon.

In the spiropyran composite, spiropyran and the polymer, inorganic material or mixture thereof may be bound to each other at a weight ratio of 0.001-5:100, particularly 0.005-3:100, more particularly 0.01-1:100, and most particularly 0.05:100. Herein, when the weight ratio of spiropyran is less than 0.001, the absolute amount of spiropyran is too small to show a change in color or fluorescence properly. On the other hand, when the weight ratio of spiropyran is larger than 5, moldability and processability may be degraded.

The mechanical stimulation may include at least one selected from the group consisting of force, stress and strain.

The inner part or the surface of the spiropyran composite is partially or totally impregnated with the sensitivity-enhancing agent through a wet infiltration process to convert the spiropyran composite into a non-polar state and to induce isotropic expansion, thereby improving mechano-sensitivity significantly. Particularly, the inner part or the surface of the spiropyran composite may be totally impregnated with the sensitivity-enhancing agent. In this case, the impregnated sensitivity-enhancing agent converts the inner part of the spiropyran composite into non-polar environment to induce an equilibrium state in which spiropyran (SP) is more stable than merocyanine (MC), and reduces an initial change in color and fluorescence of the spiropyran composite, thereby improving mechano-sensitivity.

In addition, the spiropyran composite may be expanded isotropically and uniformly to induce uniform pre-stretch, thereby making the activation onset, where a change in color or fluorescence of the spiropyran composite is started, earlier, while increasing the activation slope of a change in color or fluorescence in response to strain. In this manner, a change in color or fluorescence to mechano-sensitivity appears clearly and vividly so that it may be detected easily by the naked eyes.

Particularly, the sensitivity-enhancing agent may have a relative dielectric constant of 33 or less, may be at least one selected from the group consisting of a non-polar solvent, an organic material and an inorganic material, and more particularly, may be a non-polar solvent. Herein, 'relative dielectric constant' is a macro-measure for the dipole moment of a molecule, and a higher relative dielectric constant suggests higher polarity. For example, water may have a relative dielectric constant of about 79, and methanol and hexane may have a relative dielectric constant of 33 and 2, respectively.

Particularly, the non-polar solvent may be at least one selected from the group consisting of methanol, ethanol, isopropyl alcohol, acetone, benzophenone, methyl ethyl ketone, diethylene glycol, pyridine, dichloroethane, methylene chloride, tetrahydrofuran, dimethoxyethane, diethylene glycol dimethyl ether, acetic acid, ethyl acetate, chlorobenzene, chloroform, ether, xylene, triethylamine, toluene, carbon tetrachloride, dioxane, benzene, cyclohexane, heptane, hexane and pentane. More particularly, the non-polar solvent may be at least one selected from the group consisting of xylene, toluene, acetone, benzene and hexane.

The organic material may be at least one selected from the group consisting of nylon, carbonate, ethylene terephthalate, ester, ether, phenol, ethylene, vinyl chloride, styrene, acrylate, methacrylate, propylene, isoprene, acrylonitrile butadiene styrene (ABS), butadiene, isobutyrene, epoxy, urethane, caprolactone, vinyl alcohol, polytetrafluoroethylene (PTFE), perfluoroalkoxyalkane (PFA), fluorine ethylene propylene (FEP), ethylene tetrafluoroethylene (ETFE), polyvinylidene fluoride (PVDF), silicone, citrate, castor oil, palm oil, starch and sugar. Particularly, the organic material may be at least one selected from the group consisting of acrylate, epoxy, urethane, caprolactone and silicone.

The inorganic material may be at least one selected from the group consisting of silica, alumina, titanium oxide, talc and mercury, particularly, silica.

The spiropyran composite may be impregnated with the sensitivity-enhancing agent at a volume ratio of the spiropyran composite and sensitivity-enhancing agent of 1:1.1-2.0, particularly 1:1.18-1.9, more particularly 1:1.38-1.8, and most particularly 1:1.55-1.75. Specifically, when the volume ratio of the sensitivity-enhancing agent is less than 1.1, the spiropyran composite undergoes little pre-stretch, and thus it is not possible to make the activation onset earlier. On the other hand, when the volume ratio of the sensitivity-enhancing agent is larger than 2.0, pre-stretch reaches the limit, and thus it is difficult to make the activation onset earlier.

The spiropyran composite may have a strain sensitivity factor of 0.5-2.5, particularly 1.2-2.5, and most particularly 2.1-2.5, as calculated by the following Mathematical Formula 1:

$$\text{strain sensitivity factor} = \frac{(\Delta I/I_0)}{\varepsilon^{ut}} \qquad \text{[Mathematical Formula 1]}$$

wherein $I_0$ represents the initial fluorescence intensity, $\Delta I$ represents a change in fluorescence intensity, and $\varepsilon^{ut}$ represents a strain ratio.

Particularly, although it is not described clearly in the following Examples and Comparative Examples, in the spiropyran composite according to the present disclosure, spiropyran composites obtained by using the following seven different conditions were used to manufacture damage detection sensors, and then the mechano-sensitivity of each sensor was evaluated by applying mechanical stimulation of force, stress or strain for 300 hours at regular intervals.

As a result, it is shown that when the following conditions are totally satisfied, mechanical stimulation applied at regular intervals causes a change in color or fluorescence so that it may be clearly seen by the naked eyes for 300 hours, unlike the other conditions and the other numerical ranges, and thus the sensor can be used for a long time:

1) The spiropyran composite includes spiropyran, and a polymer bound covalently to the spiropyran, 2) the polymer is polydimethyl siloxane, 3) the spiropyran and polymer are bound to each other at a weight ratio of 0.01-1:100, 4) the spiropyran composite is impregnated with the sensitivity-enhancing agent at a volume ratio of the spiropyran composite and sensitivity-enhancing agent of 1:1.55-1.75, 5) the sensitivity-enhancing agent is a non-polar solvent, 6) the non-polar solvent is xylene, 7) the spiropyran composite has a strain sensitivity factor of 2.1-2.5, as calculated by the following Mathematical Formula 1:

$$\text{strain sensitivity factor} = \frac{(\Delta I/I_0)}{\varepsilon^{ut}} \qquad \text{[Mathematical Formula 1]}$$

wherein $I_0$ represents the initial fluorescence intensity, $\Delta I$ represents a change in fluorescence intensity, and $\varepsilon^{ut}$ represents a strain ratio.

However, it is shown that when any one of the above seven conditions is not satisfied, a change in color or fluorescence in response to mechanical stimulation applied at regular intervals becomes faint so that it may not be distinguished clearly by the naked eyes, and thus the sensor cannot be used for a long time.

In another aspect of the present disclosure, there is provided a chromic article including the spiropyran composite.

The chromic article may be a damage detection sensor, fluorescence display sensor or artificial skin which requires chromism through a change in color or fluorescence in response to force, stress or strain, but is not limited thereto.

In still another aspect of the present disclosure, there is provided a method for manufacturing a spiropyran composite, including the steps of: introducing spiropyran to a polymer, an inorganic material or a mixture thereof and carrying out curing to obtain a spiropyran composite in which a covalent bond is induced; and impregnating the inner part or the surface of the spiropyran composite with a sensitivity-enhancing agent to mechanical stimulation partially or totally by using a wet infiltration process.

In the step of forming a spiropyran composite, spiropyran is introduced during the curing of the polymer, the inorganic material or mixture thereof, and covalent bonding is induced chemically to obtain a spiropyran composite. Herein, the spiropyran and the polymer, the inorganic material or mixture thereof may be bound to each other at a weight ratio of 0.001-5:100, particularly 0.005-3:100, more particularly 0.01-1:100, and most particularly 0.05:100.

The wet infiltration process may be carried out by impregnating the spiropyran composite with a sensitivity-enhancing agent to mechanical stimulation, or by spraying a sensitivity-enhancing agent to mechanical stimulation to the spiropyran composite. Particularly, the wet infiltration process may be carried out by impregnating the spiropyran composite with a sensitivity-enhancing agent to mechanical stimulation.

In the step of impregnation with a sensitivity-enhancing agent, the impregnation time may be 1-15 minutes, particularly 5-15 minutes, more particularly 10-15 minutes, and most particularly 12-15 minutes. Herein, when the impregnation time is less than 1 minute, it is difficult to form non-polar environment at the inner part of the spiropyran composite, and pre-stretch may not be generated substantially. On the other hand, when the impregnation time is larger than 15 minutes, saturated non-polar environment is formed at the inner part of the spiropyran composite and pre-stretch is generated to the highest degree, and thus it is not possible to expect further improvement in mechano-sensitivity.

As described above, the method for manufacturing a spiropyran composite according to the present disclosure includes impregnating a spiropyran composite with a sensitivity-enhancing agent through a wet filtration process, and thus requires no expensive equipment, includes a simple process, and can be performed rapidly within several minutes to reduce the processing time. Further, the inner part of the spiropyran composite can be provided with non-polar environment by controlling the time of impregnation with the sensitivity-enhancing agent to cause pre-stretch and to increase a change in color or fluorescence in response to force, stress or strain, thereby providing significantly improved mechano-sensitivity.

The examples and experiments will now be described. The following examples and experiments are for illustrative purposes only and not intended to limit the scope of this disclosure.

EXAMPLE 1

Manufacture of Spiropyran Composite (SP-PDMS)

As a polymer, commercially available polydimethyl siloxane (PDMS), Sylgard® (Dow Corning) was used. While polydimethyl siloxane (PDMS) was cured, spiropyran sensor molecules were introduced and covalent bonding was induced chemically to obtain a spiropyran composite (SP-PDMS) plate. Herein, spiropyran and polydimethyl siloxane were mixed at a weight ratio of 0.05:100. The resultant SP-PDMS plate was cut into a dog-bone shape by using a laser cutting system available from Universal Laser Systems. As a sensitivity-enhancing agent, a non-polar solvent, xylene, was used, and the infiltrated amount of solvent was controlled through the impregnation time. The SP-PDMS plate was impregnated with xylene as a solvent for 0, 1, 5, 10 and 15 minutes to obtain a SP-PDMS plate including xylene solvent infiltrated to the inner part thereof through a wet infiltration process.

TEST EXAMPLE 1

Change in Color and Size Depending on Solvent Impregnation Time of Spiropyran Composite (SP-PDMS)

The spiropyran composite (SP-PDMS) obtained from Example 1 was subjected to photomechanical analysis to determine a change in color and size depending on the solvent impregnation time. Since the SP-PDMS plate undergoes isotropic expansion during the infiltration of the solvent, the volume expansion ratio was calculated by cubing the strain ratio. The SP-PDMS plate was strained monoaxially at a constant tensile rate trough Instron 5587 multifunctional material tester equipped with a load cell having a capacity of 100 N. In order to minimize sliding caused by a decrease in thickness of the plate during the tensile test, a pneumatic grip was used. All of the strain test was carried out at a tensile rate of 0.007 $s^{-1}$ and at a temperature of 25° C. To determine the fluorescence intensity emitted from SP-PDMS during the tensile test, a CCD camera, Prosilica GT2750 model available from Allied Vision was used to take a single-color photograph at an interval of 2.5 seconds. In addition, ImageJ software was used to quantize the fluorescence intensity of a region of interest. The result is shown in FIGS. 2A and 2B.

Figure 2A:
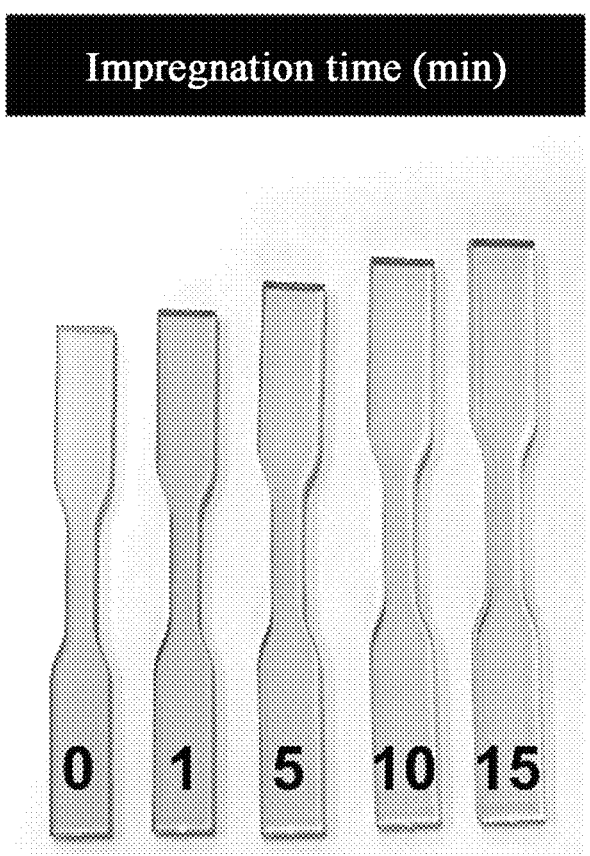
FIG. 2A illustrates the results of an initial color change and FIG. 2B shows volume ratio of the spiropyran composite (SP-PDMS) plate according to Example 1 depending on the solvent impregnation time.
Figure 2B:
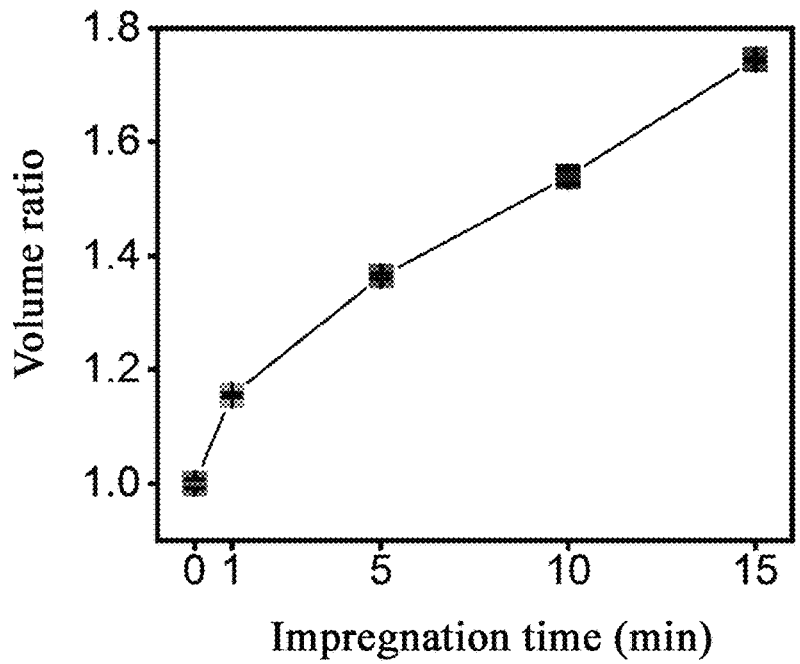

FIG. 2A illustrates the results of an initial color change and FIG. 2B shows volume ratio of the spiropyran composite (SP-PDMS) plate according to Example 1 depending on the solvent impregnation time. Referring to FIG. 2A, as the solvent impregnation time is increased in the order of 0, 1, 5, 10 and 15 minutes, the amount of xylene absorbed to the plate is increased to cause an increase in length, width and thickness of the plate. In addition, it can be seen that the color of the spiropyran composite (SP-PDMS) is changed from a purple (or blue) color into a light yellow color (or colorless), as the impregnation time is increased. This is because spiropyran is present in the form of spiropyran (colorless or light yellow) rather than merocyanine (purple or blue) under non-polar solvent environment, such as xylene.

In addition, FIG. 2B illustrates a change in volume of the spiropyran composite (SP-PDMS) depending on the solvent impregnation time. As the solvent impregnation time is increased in the order of 0, 1, 5, 10 and 15 minutes, the spiropyran composite and the solvent undergo an increase in volume ratio of 1:1.0, 1:1.8, 1:1.38, 1:1.55 and 1:1.75, respectively. Particularly, rapid expansion occurs until about 1 minute, and then an approximately linear volume change appears until 15 minutes. In the case of the plate impregnated for 15 minutes, it can be seen that the volume ratio is increased to 1:1.75.

TEST EXAMPLE 2

Evaluation of Mechano-Sensitivity Depending on Solvent Impregnation Time of Spiropyran Composite (SP-PDMS)

To determine a change in mechano-sensitivity of the spiropyran composite (SP-PDMS) plate according to Example 1, the mechano-sensitivity was calculated by the following Mathematical Formula 1, and the calculated value was defined as a strain sensitivity factor. The result is shown in FIG. 3.

$$\text{strain sensitivity factor} = \frac{(\Delta I/I_0)}{\varepsilon^{ut}} \quad [\text{Mathematical Formula 1}]$$

wherein $I_0$ represents the initial fluorescence intensity, $\Delta I$ represents a change in fluorescence intensity, and $\varepsilon^{ut}$ represents a strain ratio.

Figure 3:
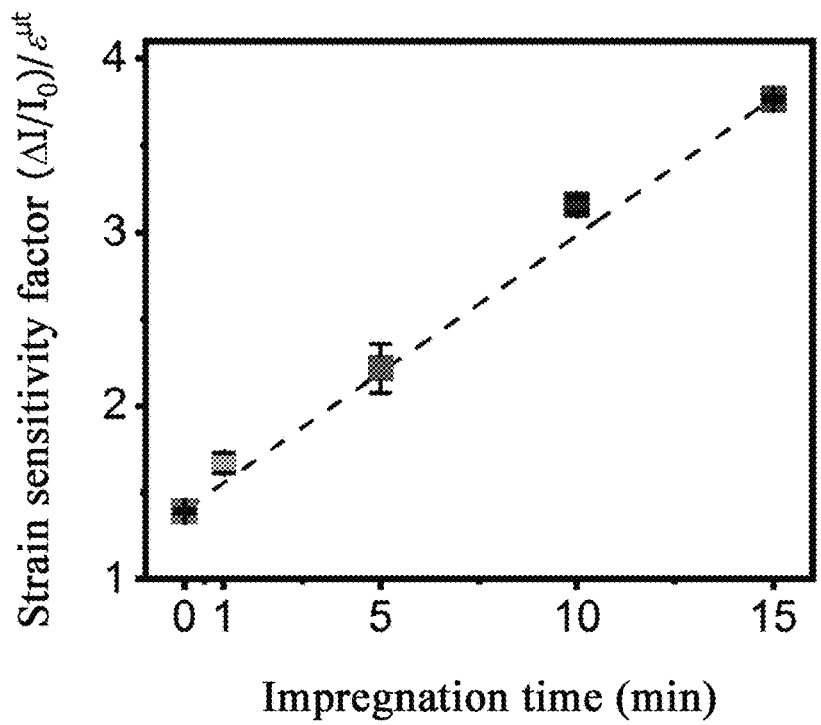
FIG. 3 is a graph illustrating the result of a change in strain sensitivity factor of the spiropyran composite (SP-PDMS) plate according to Example 1 depending on the solvent impregnation time.

FIG. 3 is a graph illustrating the result of a change in strain sensitivity factor of the spiropyran composite (SP-PDMS) plate according to Example 1 depending on the solvent impregnation time. Referring to FIG. 3, the strain sensitivity factor is increased in the order of 0.3, 0.5, 1.2, 2.1 and 2.5, as the solvent impregnation time is increased in the order of 0, 1, 5, 10 and 15 minutes. In other words, a linear increase in strain sensitivity factor is shown. Particularly, in the case of the spiropyran composite (SP-PDMS) plate subjected to impregnation for 15 minutes, the strain sensitivity factor is significantly improved to about 830% as compared to the mechano-sensitivity of the non-impregnated spiropyran composite (SP-PDMS) plate (0 minute).

TEST EXAMPLE 3

Analysis of Mechanism of Improvement in Sensitivity Depending on Solvent Impregnation Time of Spiropyran Composite (SP-PDMS)

The spiropyran composite (SP-PDMS) according to Example 1 was analyzed in terms of a change in strain sensitivity factor depending on the solvent impregnation time according to the following three mechanisms. The result is shown in FIGS. 4A to 4C.

Figure 4A:
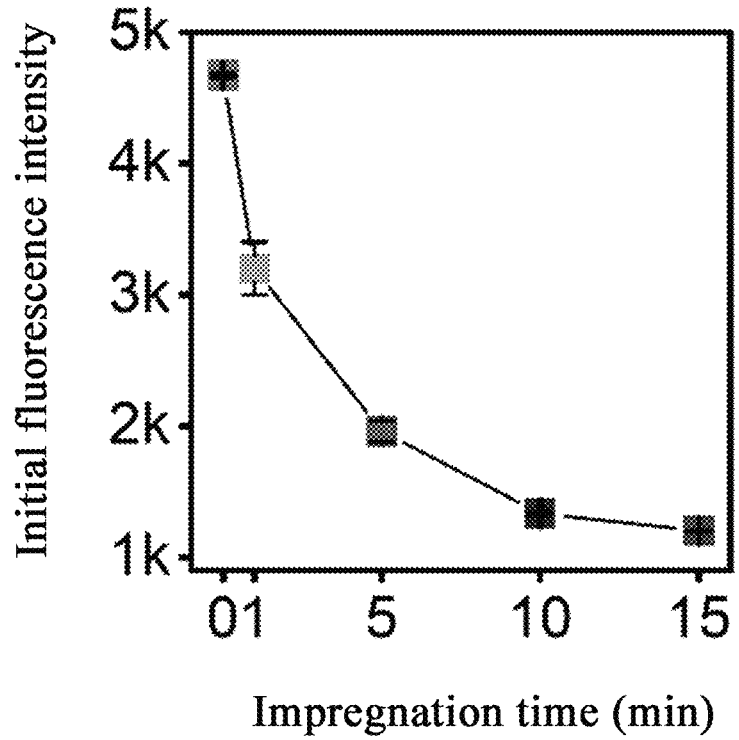
FIGS. 4A to 4C are graphs illustrating the results of a change in initial fluorescence intensity (FIG. 4A), activation onset (FIG. 4B) and fluorescence change gradient (FIG. 4C) of the spiropyran composite (SP-PDMS) plate according to Example 1 depending on the solvent impregnation time.
Figure 4B:
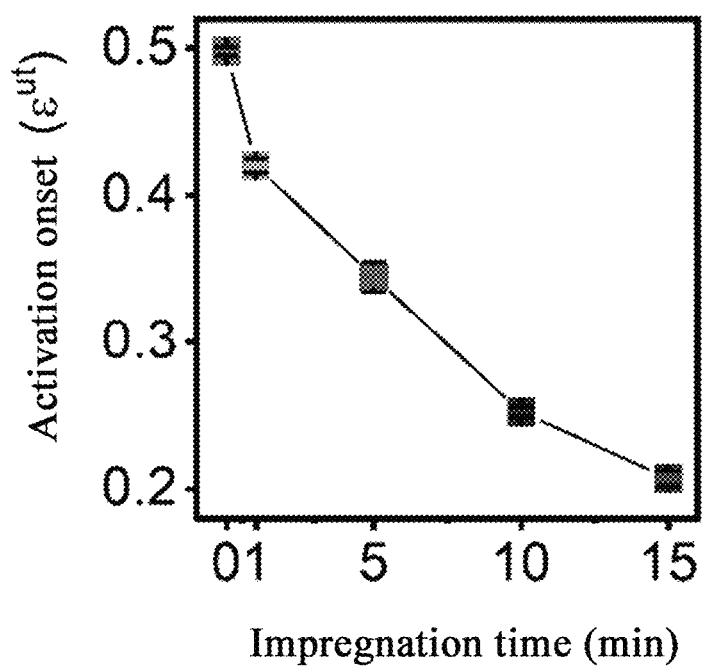
Figure 4C:
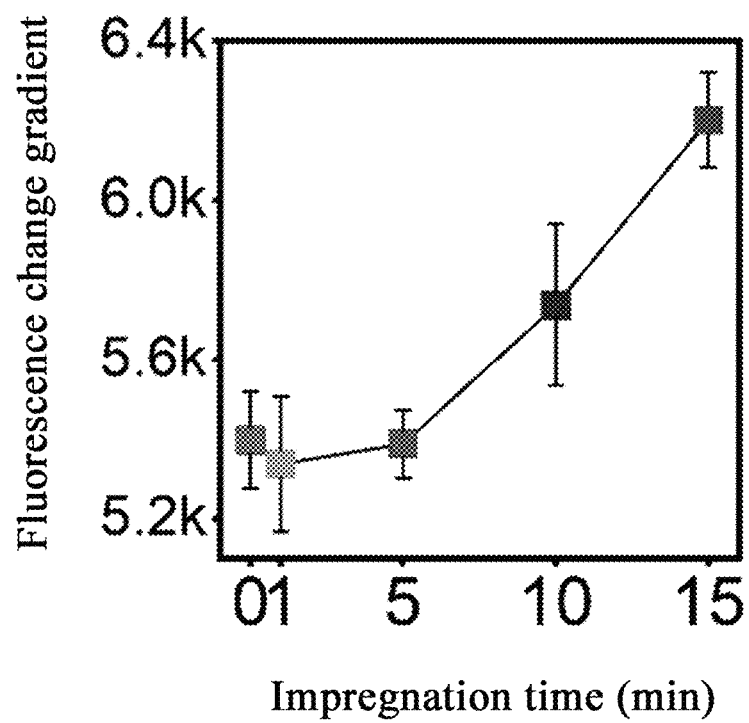

FIGS. 4A to 4C are graphs illustrating the results of a change in initial fluorescence intensity (FIG. 4A), activation onset (FIG. 4B) and fluorescence change gradient (FIG. 4C) of the spiropyran composite (SP-PDMS) plate according to Example 1 depending on the solvent impregnation time. Referring to FIG. 4A, the infiltrated solvent changes the chemical environmental of the inner part of the spiropyran composite into non-polar environment so that spiropyran (SP) may be more stable than merocyanine (MC). In other words, as the solvent impregnation time is increased, a larger amount of xylene infiltrates into the spiropyran composite to form more non-polar environment in the composite, and the amount of merocyanine (MC) showing fluorescence is reduced and the amount of spiropyran (SP) is increased, resulting in a significant decrease in initial fluorescence value. Such a decrease in initial fluorescence value further improves mechano-sensitivity.

Referring to FIG. 4B, it can be seen that as the solvent impregnation time is increased, the infiltrated solvent affects pre-stretch caused by the expansion of the spiropyran composite (SP-PDMS), and thus makes the activation onset earlier and shows an increased fluorescence change slope. This suggests that the solvent causes isotropic expansion of the polymer material itself, and the spiropyran molecule is internally subjected to force even in a state free from external force applied thereto, and thus a change in color and fluorescence may be realized with ease under a lower level of force as compared to the spiropyran composite before solvent impregnation.

Referring to FIG. 4C, it can be seen that as the solvent impregnation time is increased, a slope of change in color and fluorescence in response to strain is increased. When the solvent is infiltrated, a change in color or fluorescence is increased under the same strain, which may positively affect improvement of the sensitivity. It can be seen from the above result that improvement of mechano-sensitivity derived from solvent infiltration is caused by a decrease in initial fluorescence intensity, a decrease in activation onset and an increase in fluorescence change slope. In other words, such mechanisms significantly increase the numerator in the strain sensitivity factor of the above Mathematical Formula 1, resulting in a significant improvement of sensitivity of 830% or more.

TEST EXAMPLE 4

Analysis of Color Development Derived from Wet Infiltration Process of Spiropyran Composite (SP-PDMS)

The spiropyran composite (SP-PDMS) plate according to Example 1 was observed in various strain modes in terms of mechano-sensitivity and a degree of color development, before impregnation (0 minute) and 15 minutes after impregnation, in order to determine the effect of the solvent infiltration process directly by the naked eyes. The result is shown in FIGS. 5A to 5C.

Figure 5A:
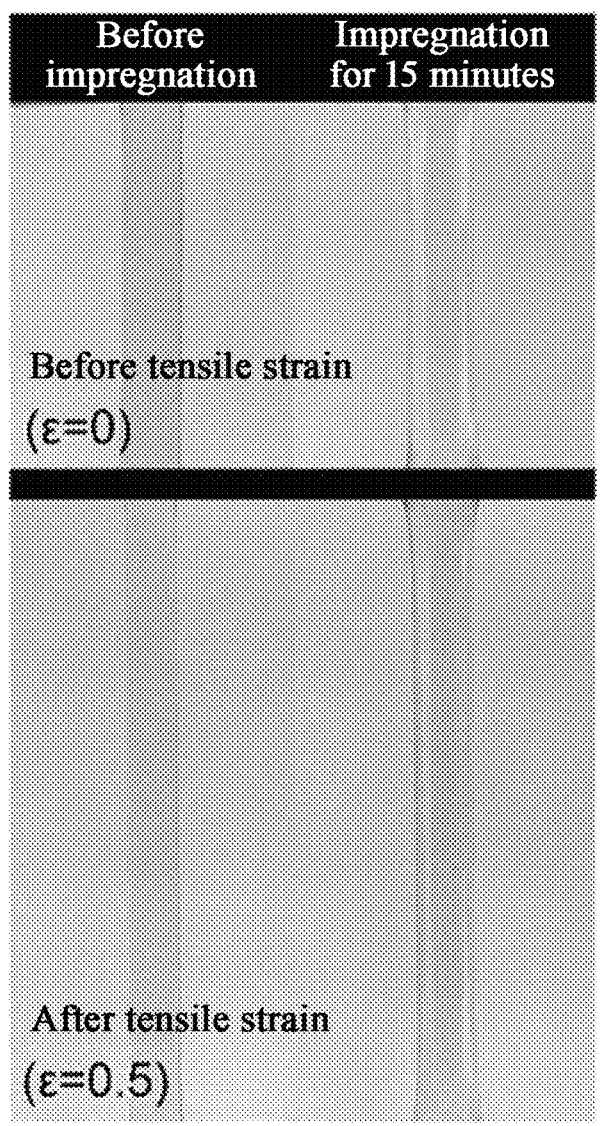
FIGS. 5A to 5C illustrate the results of mechano-sensitivity and color development degree in a tensile mode (FIG. 5A), compression mode (FIG. 5B) and bending strain mode (FIG. 5C) for the spiropyran composite (SP-PDMS) plate according to Example 1 before solvent impregnation (0 min.) and the spiropyran composite (SP-PDMS) plate 15 minutes after impregnation.
Figure 5B:
Figure 5B:
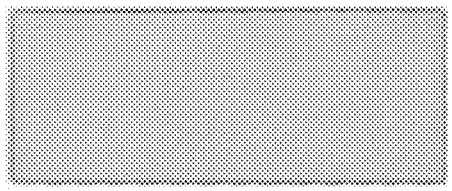
Figure 5B:
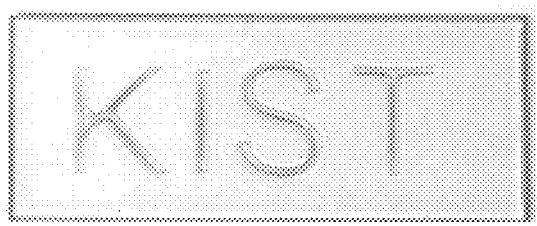
Figure 5C:
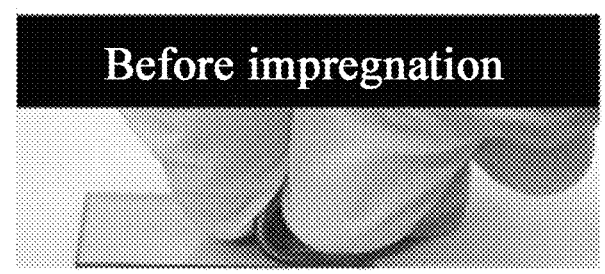
Figure 5C:
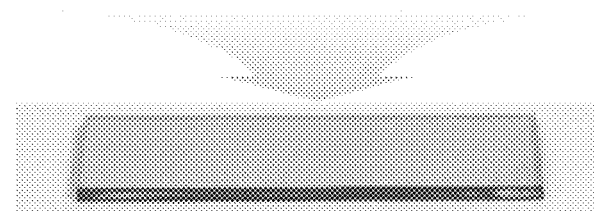
Figure 5C:
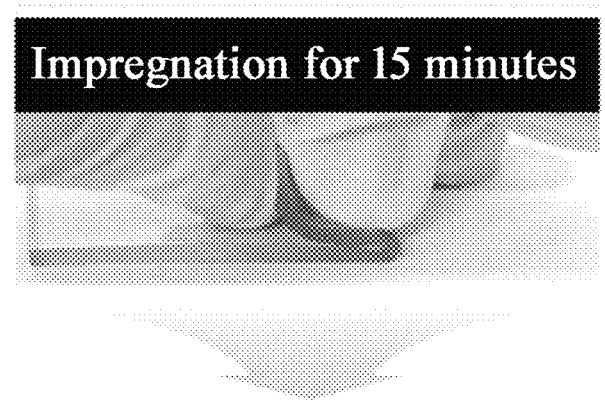
Figure 5C:

FIGS. 5A to 5C illustrate the results of mechano-sensitivity and color development degree in a tensile mode (FIG. 5A), compression mode (FIG. 5B) and bending strain mode (FIG. 5C) for the spiropyran composite (SP-PDMS) plate according to Example 1 before solvent impregnation (0 min.) and the spiropyran composite (SP-PDMS) plate 15 minutes after impregnation. Referring to FIG. 5A, the non-impregnated spiropyran composite (SP-PDMS) shows a light purple color before tensile strain and after tensile strain at $\varepsilon=0.5$, and the colors of both cases cannot be distinguished. On the contrary, in the case of the plate impregnated for 15 minutes, it shows a substantially transparent color before tensile strain, but shows a clear change in color into a blue color by mechanical activation, when being subjected to tensile strain at $\varepsilon=0.5$. Such improvement in mechano-sensitivity and color development of the spiropyran composite (SP-PDMS) can also be seen clearly in the other strain modes, i.e. compression and bending of FIGS. 5B and 5C

What is claimed is:

1. A sensitivity-enhanced spiropyran composite comprising:
   (a) spiropyran; and a polymer, an inorganic material or a mixture thereof covalently bound to the spiropyran thereby forming a spiropyran composite, and
   (b) a sensitivity enhancing agent to improve sensitivity to mechanical stimulation, partially or totally impregnated at the inner part or the surface of the spiropyran composite which converts the spiropyran composite into a non-polar state thereby forming the sensitivity-enhanced spiropyran composite,
   wherein the sensitivity enhancing agent induces isotropic expansion such that the volume ratio of the spiropyran composite prior to impregnation and the sensitivity-enhanced spiropyran composite after impregnation is 1:1.1-2.0;
   wherein the sensitivity enhancing agent is selected from a non-polar solvent, an organic material, and an inorganic material and has a relative dielectric constant of 33 or less; and
   wherein the sensitivity enhancing agent is impregnated by wet filtration into the spiropyran composite for 1-15 minutes.

2. The sensitivity-enhanced spiropyran composite according to claim 1, wherein the polymer is at least one selected from the group consisting of polydimethyl siloxane, polyurethane, polycaprolactone, polyamide, polystyrene, polyacrylate, polyaniline, epoxy, cellulose, natural rubber and derivatives thereof.

3. The sensitivity-enhanced spiropyran composite according to claim 1, wherein the inorganic material is a hydride or oxide comprising at least one selected from the group consisting of iron, aluminum, copper, tin, boron and silicon.

4. The sensitivity-enhanced spiropyran composite according to claim 1, wherein the spiropyran composite comprises spiropyran and the polymer, the inorganic material or a mixture thereof bound to each other at a weight ratio of 0.001-5:100.

5. The sensitivity-enhanced spiropyran composite according to claim 1, wherein the mechanical stimulation comprises at least one selected from the group consisting of force, stress and strain.

6. The sensitivity-enhanced spiropyran composite according to claim 1, wherein the non-polar solvent is at least one selected from the group consisting of methanol, ethanol, isopropyl alcohol, acetone, benzophenone, methyl ethyl ketone, diethylene glycol, pyridine, dichloroethane, methylene chloride, tetrahydrofuran, dimethoxyethane, diethylene glycol dimethyl ether, acetic acid, ethyl acetate, chlorobenzene, chloroform, ether, xylene, triethylamine, toluene, carbon tetrachloride, dioxane, benzene, cyclohexane, heptane, hexane and pentane.

7. The sensitivity-enhanced spiropyran composite according to claim 1, wherein the organic material is at least one selected from the group consisting of nylon, carbonate, ethylene terephthalate, ester, ether, phenol, ethylene, vinyl chloride, styrene, acrylate, methacrylate, propylene, isoprene, acrylonitrile butadiene styrene (ABS), butadiene, isobutyrene, epoxy, urethane, caprolactone, vinyl alcohol, polytetrafluoroethylene (PTFE), perfluoroalkoxyalkane (PFA), fluorine ethylene propylene (FEP), ethylene tetrafluoroethylene (ETFE), polyvinylidene fluoride (PVDF), silicone, citrate, castor oil, palm oil, starch and sugar.

8. The sensitivity-enhanced spiropyran composite according to claim 1, wherein the inorganic material is at least one selected from the group consisting of silica, alumina, titanium oxide, talc and mercury.

9. The sensitivity-enhanced spiropyran composite according to claim 1, which has a strain sensitivity factor of 0.5-2.5, as calculated by the following Mathematical Formula 1:

$$\text{strain sensitivity factor} = \frac{(\Delta I/I_0)}{\varepsilon^{ut}} \qquad \text{[Mathematical Formula 1]}$$

wherein $I_0$ represents the initial fluorescence intensity, $\Delta I$ represents a change in fluorescence intensity, and $\varepsilon^{ut}$ represents a strain ratio.

10. The sensitivity-enhanced spiropyran composite according to claim 1, wherein the spiropyran composite comprises spiropyran, and a polymer bound covalently to the spiropyran,
   the polymer is polydimethyl siloxane,
   the spiropyran and polymer are bound to each other at a weight ratio of 0.01-1:100,
   the spiropyran composite is impregnated with the sensitivity-enhancing agent at a volume ratio of the spiropyran composite and sensitivity-enhancing agent of 1:1.55-1.75,
   the sensitivity-enhancing agent is a non-polar solvent,
   the non-polar solvent is xylene, and
   the spiropyran composite has a strain sensitivity factor of 2.1-2.5, as calculated by the following Mathematical Formula 1:

$$\text{strain sensitivity factor} = \frac{(\Delta I/I_0)}{\varepsilon^{ut}} \qquad \text{[Mathematical Formula 1]}$$

wherein $I_0$ represents the initial fluorescence intensity, $\Delta I$ represents a change in fluorescence intensity, and $\varepsilon^{ut}$ represents a strain ratio.

11. A chromic article comprising the sensitivity-enhanced spiropyran composite according to claim 1.

* * * * *